United States Patent

Dawson et al.

[11] Patent Number: 5,999,850
[45] Date of Patent: Dec. 7, 1999

[54] PACEMAKER WITH SAFE R-WAVE SYNCHRONIZATION DURING COUNTERSHOCK CONVERSION OF ATRIAL FIBRILLATION

[75] Inventors: Albert Dawson, Littleton; Saul E. Greenhut, Aurora, both of Colo.

[73] Assignee: Pacesetter, Inc., Sylmar, Calif.

[21] Appl. No.: 08/897,292

[22] Filed: Jul. 21, 1997

[51] Int. Cl.⁶ .................................................. A61N 1/39
[52] U.S. Cl. ................................................................ 607/4
[58] Field of Search ................................ 607/4, 9, 14, 25

[56] References Cited

U.S. PATENT DOCUMENTS

| | | |
|---|---|---|
| 4,766,901 | 8/1988 | Callaghan . |
| 5,207,219 | 5/1993 | Adams et al. . |
| 5,411,524 | 5/1995 | Rahul ........................................... 607/4 |
| 5,441,523 | 8/1995 | Nappholz ................................... 607/14 |
| 5,480,413 | 1/1996 | Greenhut et al. .......................... 607/14 |
| 5,591,215 | 1/1997 | Greenhut et al. .......................... 607/14 |

*Primary Examiner*—Jeffrey R. Jastrzab
*Attorney, Agent, or Firm*—Gottlieb, Rackman & Reisman, P.C.

[57] ABSTRACT

An implantable atrial defibrillator analyzes both the atrium and the ventricle to determine an abnormal atrial condition of the atrium and if the ventricle is unstable. Therapy is applied to correct the abnormal atrial condition, such as atrial fibrillation, only if the ventricle is stable, to insure that the therapy does not provoke a ventricular tachyarrhythmia. If the ventricle is unstable, first a process is performed to stabilize it, for example by using a ventricular pacing protocol. After the ventricle is stabilized, the atrial therapy is applied in synchronism with the ventricular events (i.e., in synchronism with either ventricular intrinsic events or ventricular pacing pulses.)

25 Claims, 5 Drawing Sheets

PACEMAKER WITH SAFE R-WAVE SYNCHRONIZATION DURING COUNTERSHOCK CONVERSION OF ATRIAL FIBRILLATION

BACKGROUND OF THE INVENTION a. Field of Invention

This invention pertains to an implantable pacemaker and more particularly to a pacemaker constructed and arranged to provide therapy for atrial fibrillation. More particularly, this invention pertains to a pacemaker having means for providing atrial defibrillation using defibrillation pulses applied precisely in synchronism with ventricular activity. Moreover the invention also pertains to an implantable atrial defibrillator which monitors the ventricle and stabilizes the same if necessary, before the application of atrial defibrillation pulses.

b. Description of the Prior Art

Since ventricular tachyarrhythmias can have grave and potentially lethal consequences, the primary concern for clinicians and pacemaker manufacturers until recently has been the detection and reversion of this undesirable condition. While many pacemakers were also capable of detecting atrial fibrillation, this latter condition was believed to be relatively benign, if unpleasant to the patient. Accordingly, atrial fibrillation was originally either ignored, or treated in a palliative manner.

However, since present pacemakers are capable of handling ventricular arrhythmia, attention has turned toward the detection and treatment of atrial fibrillation. There are several reasons why it is thought to be important to control atrial fibrillation. First, atrial fibrillation is associated with the loss of AV synchrony and therefore can result in a fast and irregular heart rate causing hemodynamically inefficient cardiac operation. Atrial fibrillation has also been associated with other symptoms such as dyspnea, fatigue, vertigo, angina pectoris, and palpitations. These conditions may lead to a patient losing his ability to enjoy life, perform work, and function normally. Atrial fibrillation is also a significant cause of stroke and death, via emboli arising from the left atrium.

Recent studies have shown in fact that atrial fibrillation occurs in 0.3–0.4% of the general population. Moreover, the incidence of atrial fibrillation increases with age, so that it reaches 2–4% by the age 60, and 8–11% for patients above 75 years old.

Drug therapy and/or in-hospital cardioversion are the current clinical therapies provided for atrial defibrillation. However, these approaches are of limited efficacy. Hence, implantable atrial defibrillators (IADs) have been proposed as one of several non-pharmacologic therapeutic options. See for instance U.S. Pat. No. 5,207,219. Studies have shown that internal atrial defibrillation is feasible at low energy levels. This feature is important for IADs because if the defibrillation pulses are successful at low energy, they can be relatively painless and therefore desirable for treating a conscious patient with atrial fibrillation. However one problem with the IADs proposed so far is that it can be difficult to synchronize their defibrillation pulses to the intrinsic ventricular events, because the ventricular rate can be highly variable. If atrial defibrillation pulses are not carefully synchronized with the ventricular intrinsic events, then a ventricular tachyarrhythmia (e.g., ventricular fibrillation) could be induced. Thus, rather then helping the patient, the present IADs may have a negative effect, namely inducement of ventricular arrhythmia. IADs are desirable because they may reduce the number and duration of AF episodes, may improve the lifestyle of the patient, may reduce the number of hospitalizations for treatment of recurring atrial fibrillation and may reduce morbidity and mortality. However, in a device without ventricular defibrillation capability, any instance of ventricular arrhythmia inducement by the IAD is unacceptable. IADs may be designed, in fact, as a dual chamber defibrillator with defibrillation capability in the atrium and ventricle. Even so, it is desirable to greatly minimize the induction of ventricular tachyarrhythmias by the devices.

OBJECTIVES AND SUMMARY OF THE INVENTION

In view of above, it is an objective of the present invention to provide an implantable atrial defibrillator which is arranged and constructed to stabilize the ventricular rate before atrial defibrillation therapy is applied.

A further objective is to provide a device which is readily integrated, if desired, with a single or dual chamber implantable pacemaker.

Yet a further objective is to provide an atrial defibrillator which has optimal synchronization to either paced or intrinsic ventricular events.

Other objectives and advantages of the invention shall become apparent from the following description. Briefly, an atrial defibrillator constructed in accordance with this invention includes an atrial sensor or monitor for sensing an abnormal atrial condition such as atrial fibrillation, and a ventricular rate stabilizer to stabilize the ventricular rate. If the ventricle is found to be stable then the therapy for converting the atrial abnormal condition is applied in synchrony with ventricular events (i.e., intrinsic ventricular beats or pacing pulses) to insure that the therapy does not cause a ventricular tachyarrhythmia. If the ventricle is unstable, then a ventricular stabilizing procedure is initiated to stabilize the ventricle before the atrial therapy is applied. Preferably the ventricle is stabilized by pacing it until a stable ventricular rate is achieved.

More specifically, once AF is detected and confirmed via algorithms known in the art (see U.S. patent application Ser. No. 730,748 filed Oct. 15, 1996, entitled PACEMAKER WITH IMPROVED DETECTION OF ATRIAL FIBRILLATION, now U.S. Pat. No. 5,720,295, and incorporated herein by reference), a ventricular rate stabilizing algorithm (for example, as in U.S. Pat. No. 5,480,413 incorporated herein by reference) is activated. After a suitable time has passed so that the ventricular rate has been stabilized (e.g. 3 min.) then the therapy for converting the atrial abnormal condition is applied in synchrony with a ventricular event (intrinsic ventricular depolarization or pacing pulse) to insure that therapy does not cause a ventricular arrhythmia. According to U.S. Pat. No. 5,480,413 the ventricular pacing rate may be below the maximum intrinsic ventricular (V) rate. In addition to stabilizing the ventricular rate, a check may be made to insure that the atrial defibrillator therapy does not occur following a short V—V interval. It is thought that by stabilizing the ventricular rate by pacing, the potential for ventricular arrhythmia induction will be reduced.

DETAILED DESCRIPTION OF THE INVENTION

In the following description, a combined implantable defibrillator/pacemaker is illustrated, it being understood that some of the functionality of the pacemaker may be omitted if desired. For the sake of simplicity, the device is generically referred to as a pacemaker.

Figure 1:
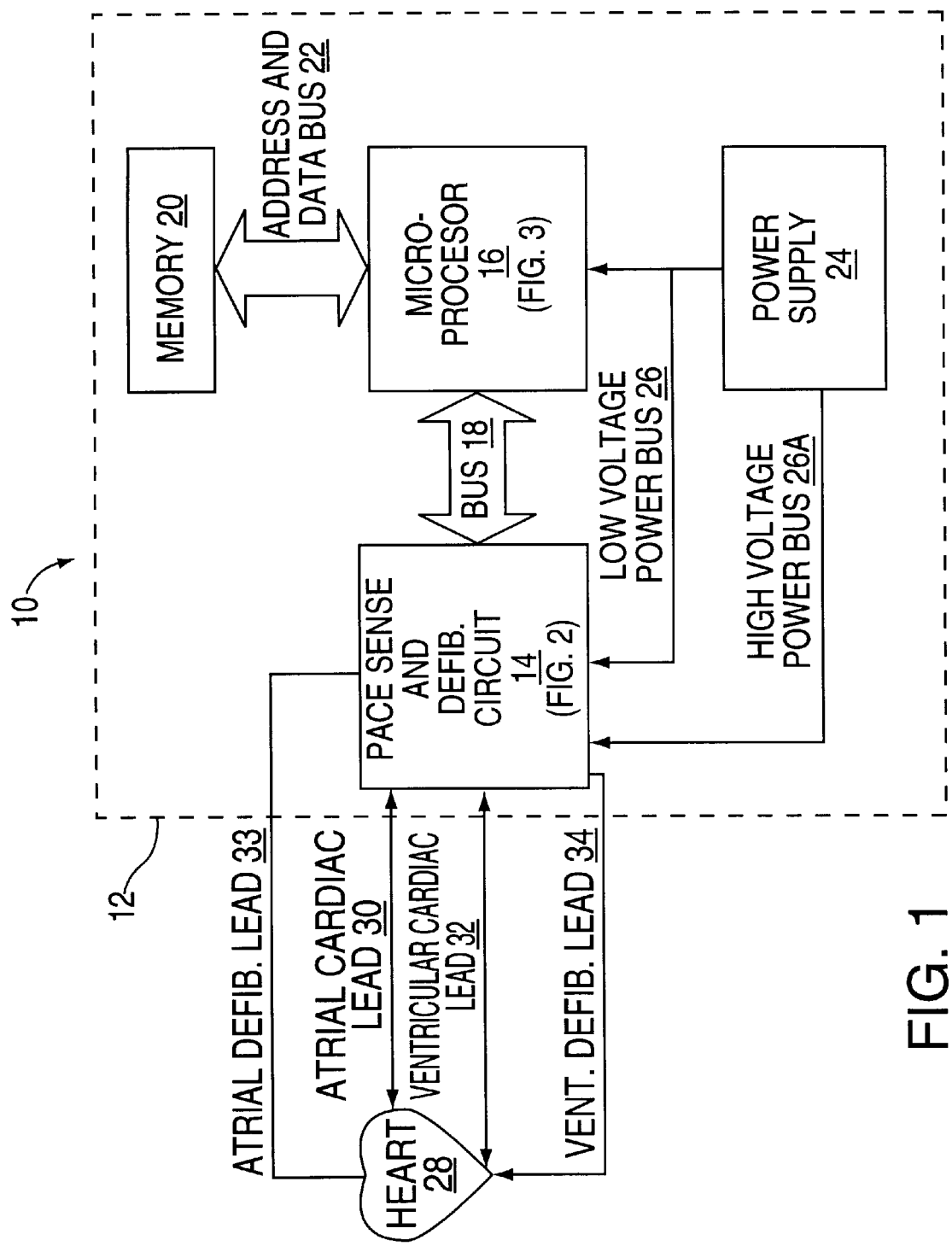
FIG. 1 shows a block diagram for an atrial defibrillator constructed in accordance with this invention.

Referring now to FIG. 1, a pacemaker 10 constructed in accordance with this invention includes an implantable housing 12. The housing holds a pace, sense and defibrillator circuit 14, described in more detail in FIG. 2, and a microprocessor 16, described in more detail in FIG. 3. The circuit 14 and the microprocessor 16 are interconnected by a bus 18 for exchanging data, as well as communication and control signals. The pacemaker 10 further includes a memory 20 connected to the microprocessor 16 by a data and address bus 22, and a power supply 24 providing low voltage power to the various pacing components of pacemaker 10 via low voltage power bus 26. In addition, power supply 24 further provides a high voltage power bus 26A which is used to provide the energy for the defibrillation pulses.

Once implanted, the pacemaker 10 is connected to a patient's heart 28 by leads 30, 32, 33 and 34. Preferably, leads 30, 32 are bi-polar leads with lead 30 being connected to the atrial chamber of the heart, and lead 32 being connected to the ventricular chamber. Therefore leads 30 and 32 are known as the atrial cardiac lead and the ventricular cardiac lead, respectively. Lead 33 is also connected to an atrial chamber and is used to provide atrial defibrillation pulses as discussed more fully below. The atrial defibrillation electrode (not shown) may be a coronary sinus electrode terminating in the left atrium, or it may terminate in the right atrium. The atrial defibrillation pulses may be delivered between the two atrial leads or, alternatively, the atrial defibrillation pulses may be delivered through a single atrial pacing lead.

Similarly, lead 34 is connected to a ventricular defibrillation electrode (not shown) for delivering ventricular defibrillation pulses.

It should be understood that the arrangement of the pacemaker 10 and leads 30, 32, 33, 34 do not form a part of this invention. Other arrangements may be used as well, using other types of leads including tri-polar leads, unipolar leads and so on. In some embodiments, lead 30 may be absent or may only sense (not pace). For example, lead 32 may be used as a "single-pass" lead with electrodes in the atrium and ventricle.

Figure 2:
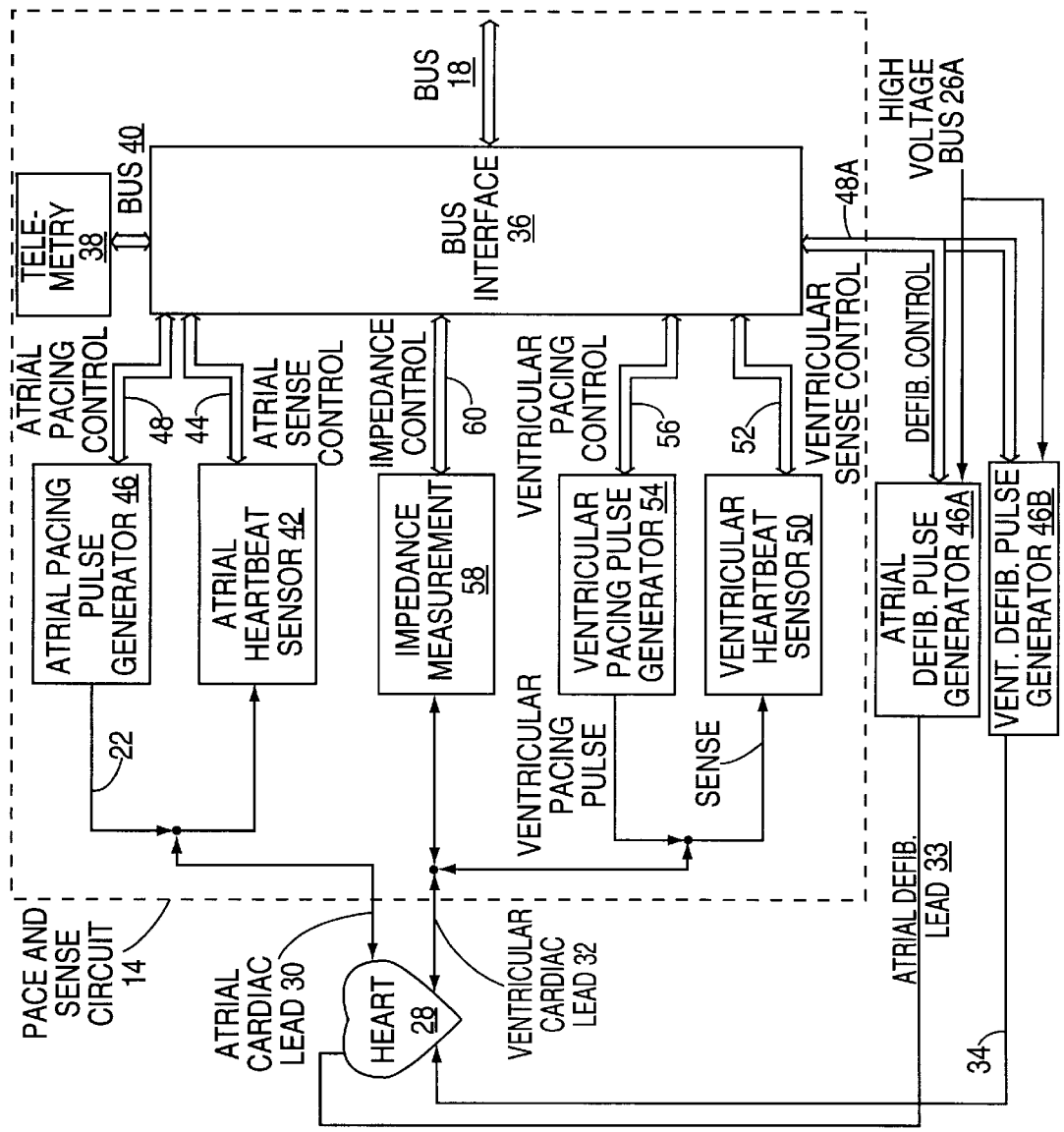
FIG. 2 shows details of the pacing, sense and defibrillator circuit of FIG. 1.

Referring now to FIG. 2, the pace and sense control circuit 14 includes a bus interface 36, a telemetry circuit 38 and various other sensing and control circuits for sensing the status of the chambers of heart 28 and to provide appropriate pacing signals thereto. The bus interface 36 provides interfacing with microprocessor 16 via bus 18. The telemetry circuit 38 provides communication with the outside world by, for example, radio frequency. Signals with the telemetry circuit are exchanged via telemetering bus 40.

More specifically, intrinsic signals from the atrium are sensed through lead 30 by the atrial sensor 42. This sensor 42 is controlled by the atrial sense control bus 44. Atrial pacing pulses are generated for lead 30 by atrial pacing pulse generator 46. This generator is controlled by the atrial pacing control bus 48. Similarly, the ventricular chamber is sensed through lead 32 by ventricular heartbeat sensor 50, which is controlled by a ventricular sense control bus 52. Pacing pulses for the ventricular chamber are generated by the ventricular pacing pulse generator 54, controlled by the ventricular pacing control bus 56.

In addition, the impedance of the thoracic tissues is measured through one of the cardiac leads, such as lead 32, by impedance measurement circuit 58. This circuit is controlled by impedance control bus 60. All the control buses are interconnected between their respective circuits and the bus interface 36 to provide two way communication with the microprocessor 16.

Importantly, the circuit 14 further includes an atrial defibrillation pulse generator 46A. This generator 46A receives high voltage power from power supply bus 26A. The generator 46A is further connected to bus interface 36 by the defibrillation control bus 48A. The generator 46A generates atrial defibrillation pulses in response to commands received from the microprocessor 16 through bus 18, bus interface 36 and bus 48A. These defibrillator pulses are typically about 0.5–5 joules.

Similarly, a ventricular defibrillation pulse generator 46B may be provided which also receives power from power supply bus 26A and commands on bus 48A. In response to these commands, generator 46B generates ventricular defibrillator pulses on lead 34.

Figure 3:
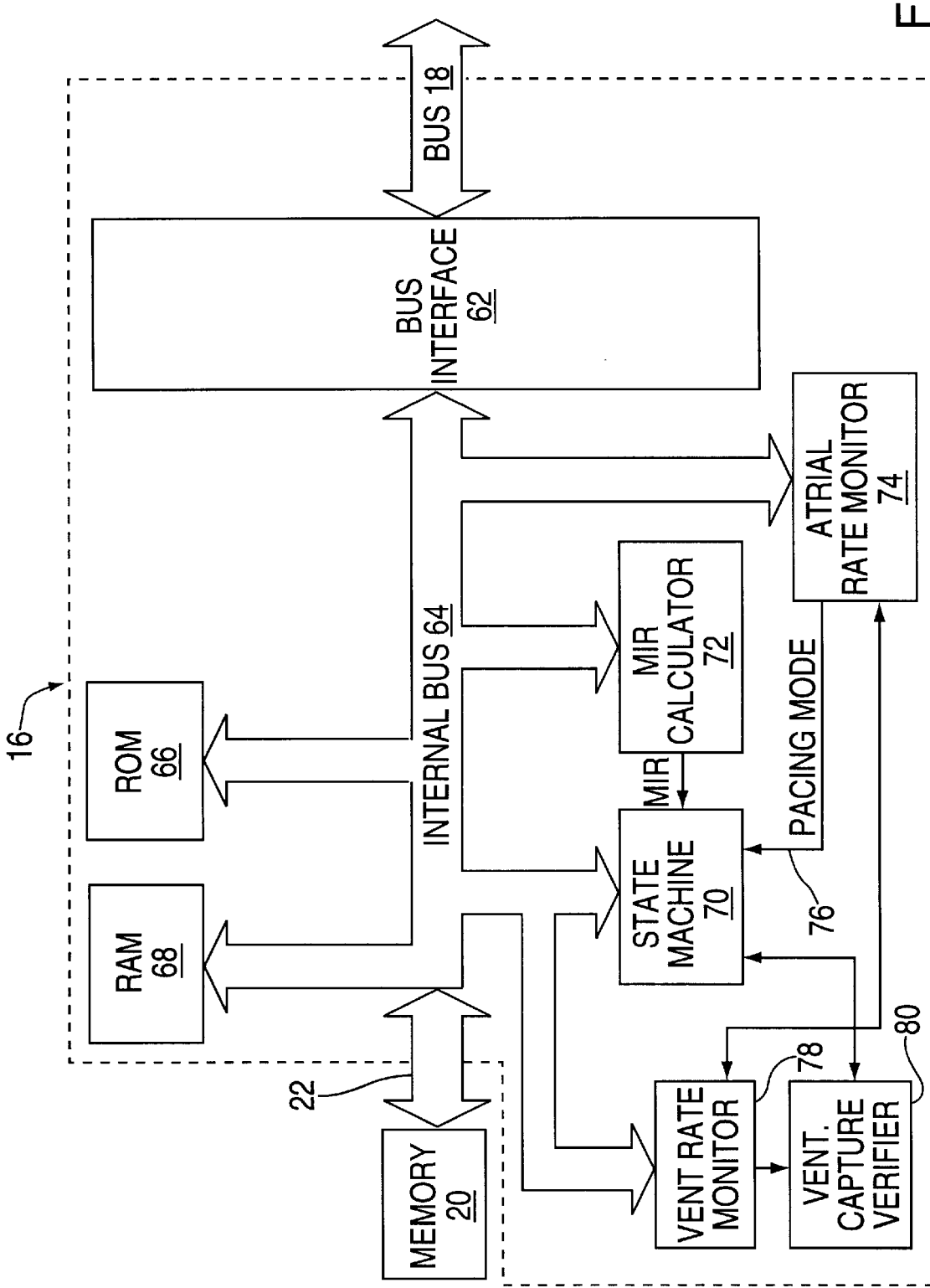
FIG. 3 shows details of the microprocessor of FIG. 1.

Referring now to FIG. 3, the microprocessor 16 includes a bus interface circuit 62 for interfacing with bus 18, and an internal bus 64 interconnecting the various components of the microprocessor 16. The microprocessor 16 further includes a read only memory (ROM) 66 used for storing programming information, a random access memory (RAM) 68 used as a scratch pad, a state machine 70, a metabolic indicated rate (MIR) calculator 72, an atrial rate monitor 74, a ventricular rate monitor 78, and a ventricular capture verifier 80.

Except as noted below, the operation of the pacemaker 10 illustrated in FIGS. 1–3 is described in commonly assigned U.S. Pat. No. 5,441,423 by T. A. Nappholz, entitled FORCED ATRIO-VENTRICULAR SYNCHRONY DUAL CHAMBER PACEMAKER, and incorporated herein by reference. Briefly, the impedance of the tissues of the thorax is measured by impedance measurement circuit 58 at regular intervals. These sequential measurements are transmitted via control bus 60, bus 18 and internal bus 64 (through the interface circuits 36 and 62) to the MIR calculator 72. This calculator 72 converts these impedance measurements into a minute volume corresponding to the patient's metabolic demand. Of course, any other Rate Responsive Sensor could be used for the purposes of this application. Alternatively, the rate responsive sensor may be omitted. This minute volume is in turn transformed into a metabolic indicated rate (MIR) and transmitted to the state machine 70. The state machine 70 also receives information regarding the sensing and/or pacing of the atrial and/or ventricular chambers of heart 28 through the respective sensors 42, 50. Based on the received information, the state machine 70 generates pacing control signals for pacing the heart in a particular mode. These control signals are transmitted to the pacing pulse generators 46 and 54 which in response generate appropriate pacing pulses to the ventricle and atrium as described above. In addition, the state machine also generates, when required, control signals for the atrial defibrillation generator 46A.

Figure 4:
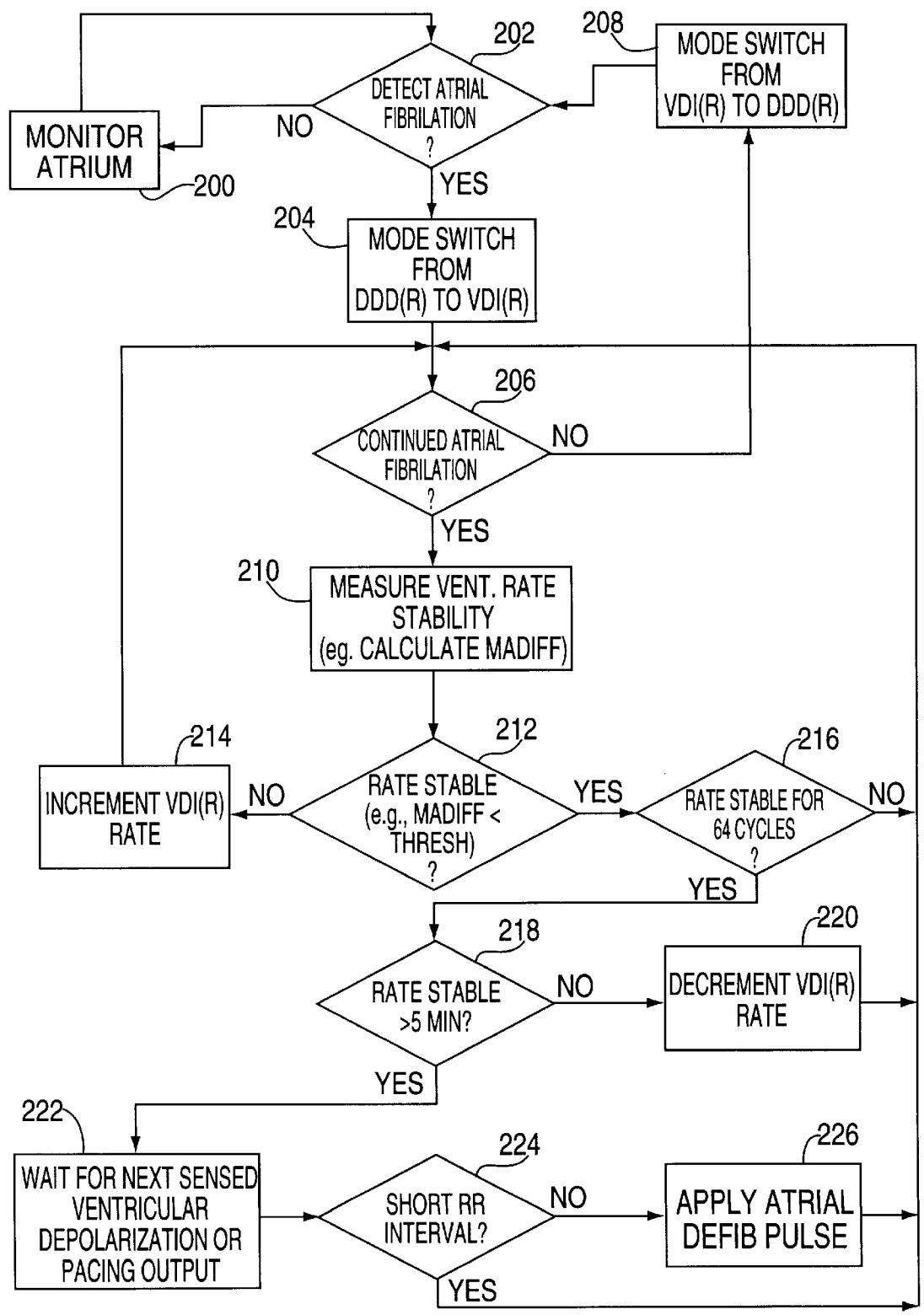
FIG. 4 shows a flow chart for applying defibrillation therapy in accordance with this invention.

The operation of the microprocessor 16 for generating these control signals shall now be described in conjunction with the Figures. Starting in FIG. 4 with step 200, the microprocessor 16 monitors the atrium, using atrial rate monitor 74. In step 202 a determination is made as to whether an atrial defibrillation episode is detected or not Methods of determining atrial defibrillation are known to one skilled in the art and need not be described in detail here. Preferred methods of detecting atrial fibrillation is found in commonly assigned U.S. application Ser. No. 730,748 filed Oct. 5, 1996, entitled PACEMAKER WITH IMPROVED DETECTION OF ATRIAL FIBRILLATION, now U.S. Pat. No. 5,720,295 and Ser. No. 805,769 filed Feb. 25, 1997 entitled "Apparatus and Method for Detecting Atrial Fibrillation by Morphological Analysis" now U.S. Pat. No. 5,817,134, both incorporated herein by reference.

If no atrial fibrillation is detected then the state machine 70 continues its standard pacing protocol defined by the preselected mode (for example DDDR) for the pacemaker, and then returns to monitoring the atrium (step 200).

If atrial fibrillation is detected in step 202, then in step 204 the atrial rate monitor sends a pacing mode command to switch the pacing mode of the state machine 70 to another (non-atrial coupled) mode such as VDI(R). In step 206, atrial monitoring continues. If atrial fibrillation ceases then in step 208, the state machine is returned to its original pacing mode (i.e., in this case, DDDR). If atrial fibrillation continues, then a measurement is made of the ventricular rate stability in step 210. The reason for this step, as discussed above, is to insure that any atrial defibrillation therapy applied to the heart will not cause a potentially fatal ventricular tachyarrhythmic episode. For example, such an undesirable event may occur if the atrial defibrillation therapy is applied while the RR interval between successive ventricular events is too short. Stabilizing the ventricular rate insures that short cycles occur less frequently and generally reduces the potential for an induced ventricular arrhythmia.

A method of measuring if the ventricular rate is stable is described in U.S. Pat. No. 5,480,413, incorporated herein by reference. If the ventricular rate is found in test 212 not to be stable, then in step 214 a preselected procedure is followed to stabilize the ventricle first, before any defibrillation therapy is applied. As described more fully in the above-mentioned U.S. Pat. No. 5,480,413, stabilization may be accomplished by adjusting the ventricular pacing rate until adequate stabilization is confirmed e.g., when ventricular rate or interval variability is reduced below a threshold.

More specifically, and as part of this mode of operation, the atrial rate is monitored by monitor 74 through sensor 42 and/or 58 and/or 50 to detect atrial tachyarrhythmias such as atrial fibrillation (AF). This may be accomplished by various methods including comparing the atrial rate to a threshold level, using waveform morphology, measuring a hemodynamic parameter, or comparing the metabolic indicated rate (MIR) with the intrinsic atrial and/or ventricular rates. If an atrial fibrillation is detected by atrial monitor 74, the microprocessor 16 enters into a ventricular rate stabilization mode. In this mode, the atrial monitor 74 sends a signal on line 76 to the state machine 70 to reset the pacing to a different mode, such as DDI, DDIR, VDI or VDIR. Next, the ventricular monitor 78 selects a new, higher ventricular pacing rate (if required to stabilize the ventricular rate) as described more fully below and sends this new rate to the pacing calculator 70.

Ventricular rate stability can be measured using a number of different methods. For example the RR interval between two R waves (standard in the pacemaker field) can be measured and the stability of this parameter may be defined in terms of statistical variance, standard deviation, root mean squared difference, normalized mean absolute deviation, normalized approximate interquartile range, autocorrelation, Markov chains, coefficient of variation, histograms, using maximum, average, and minimum values stored in a look-up table, or a normalized mean absolute difference, discussed below.

One method which is particularly advantageous is a so-called normalized mean absolute difference method described in detail below. This method is described more fully in U.S. Pat. No. 5,480,413 and is preferred because it is not very complex and hence can be easily implemented, and yet the method has the ability to accurately measure ventricular stability.

Briefly, as part of this method, the sequential RR intervals are first measured between adjacent R waves sensed in the ventricle. After such intervals are measured and assigned sequential designations $RR_1, RR_2, RR_3, \ldots RR_i$, the mean absolute difference parameter MADIFF is calculated using the formula:

$$MADIFF = \left[\sum_{i=0}^{N} |RR_{(i+1)} - RR_i|\right] / \left[\sum_{i=1}^{N} RR_i\right]$$

The numerator of this expression is obtained by taking the absolute value of the difference between adjacent $RR_i$ intervals and summing N of these differences. The denominator of this expression is obtained by adding N adjacent intervals $RR_i$. Dividing the sum of the differences by the sum of the intervals results in a parameter MADIFF, which is a normalized mean value for N intervals. This value MADIFF indicates the average variation of the intervals from an average interval after N intervals have taken place.

The parameter MADIFF is then compared to a preset threshold value. This threshold level may be for example 0.1 or 10%. A parameter value MADIFF which exceeds this threshold level is indicative of ventricular activity which is excessively variable and unstable.

While this measurement is taking place, the state machine continues to operate in the mode of operation set in step 204.

In step 212, a test is performed to determine if the ventricle stability as determined in step 210 is satisfactory. Thus, if the MADIFF parameter is calculated in step 210, in step 212, a test is performed to determine if MADIFF<THRESHOLD.

If in step 212 it is determined that the ventricular rate is unstable then in step 214 an attempt is made to stabilize the same. For instance, the pacing rate may be increased by a small amount D1 from the previous pacing rate. D1, for example, may be 5 ppm. The whole process is repeated until the ventricular rate is stabilized as determined in steps 212 and 216 for at least 64 cycles, or alternatively the atrial fibrillation spontaneously converts to sinus rhythm.

In step 218, ventricular rate stability is confirmed, for example by determining that within a running 5 minute window, the ventricular rate did not change by more than ±10 bpm. If ventricular rate stability is not confirmed then in step 220, the ventricular pacing is reduced by a small amount (i.e., 5 ppm), and the whole process is recycled.

If ventricular rate stability is confirmed in step 218, then in next step 222 the next ventricular event (either intrinsic or paced) is detected. In step 224 the current RR interval is measured. If this interval is too short, (for example less than 400 ms), then the process is repeated. If this interval exceeds an interval threshold DZ, then in step 226 an atrial defibrillation pulse is applied.

Figure 5A:
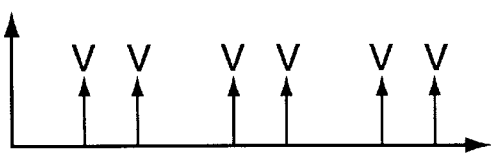
FIG. 5A shows a graph of ventricular events Vs when the ventricle is unstable.
Figure 5B:
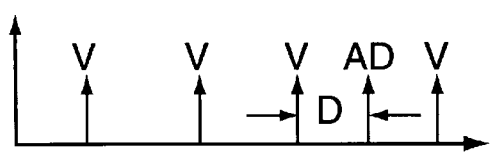
FIG. 5B shows a graph of ventricular events Vs after stabilization of the ventricle.

Prior to stabilization of the ventricle, the ventricular events V may be spaced such that their RR interval may be too short to allow (as shown in FIG. 5A) for the proper application of defibrillation therapy. However, once the ventricle is stabilized, as discussed above, the ventricular events V are spaced at relatively constant RR intervals which are normally sufficiently long enough to allow the ventricle to depolarize properly before the atrial defibrillation pulse is applied. That is, as seen in FIG. 5B, the atrial defibrillation pulse AD are applied a duration D after a ventricular event which is preferably in the range of 0–50 msec.

Figure 4A:
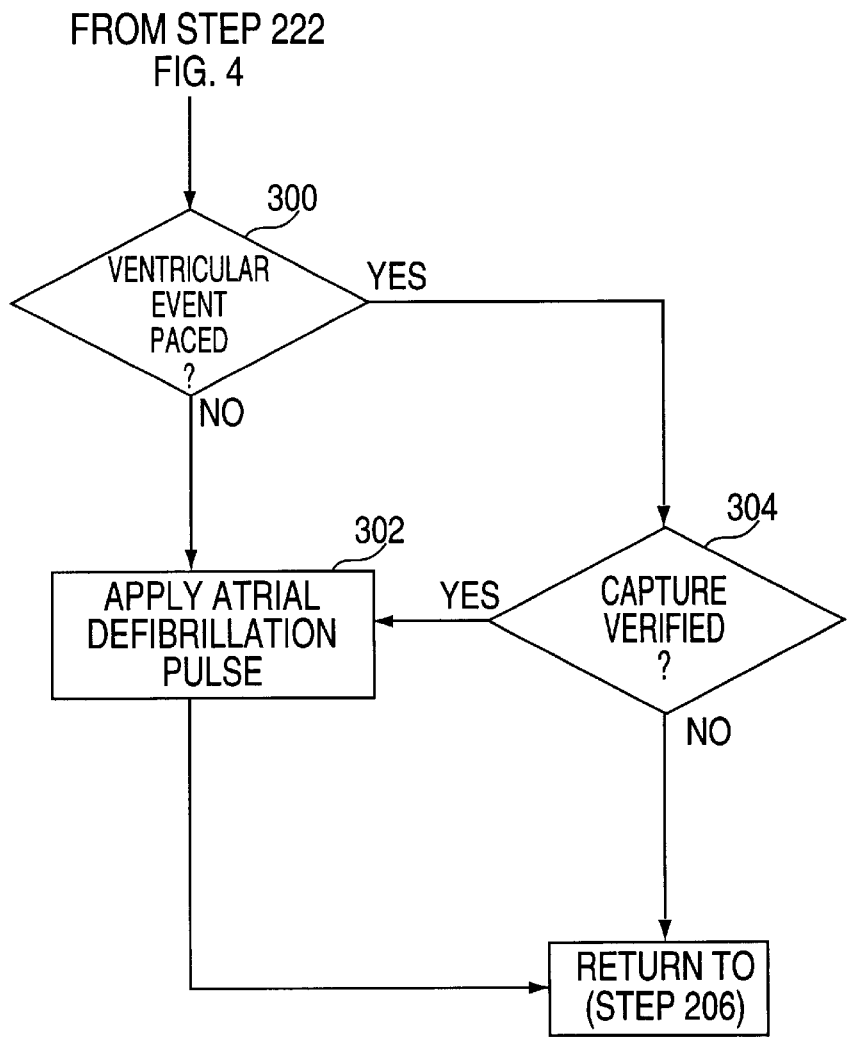
FIG. 4A shows a flow chart of an alternate embodiment of the invention.

In an alternate embodiment shown in FIG. 4A, in step 300, a check is performed to determine if the last ventricular event was a paced event. If not, then in step 302 an atrial defibrillation pulse is applied. If the last ventricular event was paced, then in step 304 ventricular capture is verified. Capture verification is well known in the art, for example from U.S. Pat. No. 4,766,901. If capture is not verified in step 304, no atrial fibrillation is applied. Capture verification is performed by ventricular capture verifier 80 of FIG. 3.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. An implantable atrial defibrillator comprising:
   an atrial sensor sensing intrinsic atrial events and generating corresponding atrial sense signals;
   a pulse generator for generating an atrial defibrillator pulse in response to a command;
   a ventricular stability sensor for sensing if the ventricular rate is stable;
   a ventricular stabilizing circuit coupled to said ventricular stability sensor and adapted to generate ventricular pacing pulses selected to stabilize said ventricle if said ventricular rate is unstable; and
   a controller including an atrial fibrillation detector responsive to said atrial sense signals, said atrial fibrillation detector being adapted to detect an atrial fibrillation based on said atrial sense signals, said controller being constructed and arranged to generate said command only when said atrial fibrillation is detected and said ventricular rate is stable.

2. The defibrillator of claim 1 further comprising a ventricular stabilizer for stabilizing said ventricular rate when said ventricular stability sensor indicates that said ventricular rate is unstable.

3. The defibrillator of claim 2 further comprising a ventricular pulse generator for generating ventricular pacing pulses and wherein said ventricular stabilizer stabilizes said ventricular rate by pacing the ventricle using said ventricular pulse generator.

4. The defibrillator of claim 1 further comprising a ventricular sensor that senses ventricular events, wherein said atrial defibrillator pulses are generated synchronously with said ventricular events.

5. The defibrillator of claim 4 wherein said ventricular events are intrinsic ventricular events.

6. The defibrillator of claim 4 wherein said ventricular events are ventricular pacing pulses.

7. An implantable atrial defibrillator comprising:
   an atrial sensor sensing intrinsic atrial events and generating corresponding atrial sense signals;
   an atrial defibrillator pulse generator that generates an atrial defibrillator pulse in response to a command;
   a ventricular pulse generator that generates ventricular pacing pulses at a predetermined ventricular rate;
   a controller generating said command; and
   a capture verification circuit for sensing if ventricular capture by said ventricular pacing pulses occurs, wherein said controller generates said command only if ventricular capture is indicated by said capture verification circuit.

8. An implantable pacemaker comprising:
   a sensor sensing intrinsic atrial events and generating corresponding atrial sense signals;
   an atrial pulse generator for generating atrial pulses in response to an atrial pace command;
   a ventricular stability determinator for determining a stability of the ventricle;
   an atrial analyzer determining an abnormal condition of the atrium based on said atrial sense signals;
   a pacing controller receiving said atrial sense signals and generating said atrial command; and
   an atrial therapy controller for applying therapy to the atrium if said abnormal conditions are detected and said ventricular rate is stable.

9. The pacemaker of claim 8 further comprising a ventricular sensor sensing intrinsic ventricular events and generating corresponding ventricular sense signals, said ventricular determinator determining said ventricular stability from said ventricular sense signals.

10. The pacemaker of claim 8 further comprising a ventricle stabilizer for stabilizing said ventricle.

11. The pacemaker of claim 10 wherein said ventricle stabilizer stabilizes the ventricle by pacing the same.

12. The pacemaker of claim 8 further comprising a ventricular sensor for sensing intrinsic ventricular events and a ventricular pace generator for generating ventricular pacing pulses in response to ventricular commands and wherein said pacing controller receives said ventricular sense signals and generates in response said ventricular commands.

13. The pacemaker of claim 12 wherein said pacing controller stabilizes said ventricle when said ventricle is unstable.

14. The pacemaker of claim 13 wherein said pacing controller stabilizes said ventricle by overdriving said ventricle.

15. The pacemaker of claim 8 further comprising a ventricular determinator for determining ventricular events, wherein said atrial therapy controller applies said therapy in synchronism with said ventricular events.

16. The pacemaker of claim 15 wherein said atrial therapy controller generates atrial defibrillation pulses, said atrial defibrillation pulses being generated a predetermined time after said ventricular events.

17. A method of defibrillating the atrium of a patient using an implantable atrial defibrillator, said method comprising the steps of:
   sensing an atrial fibrillation in the patient heart;
   determining if the ventricle is stable; and
   applying defibrillation therapy with said implantable defibrillator to the atrium if the ventricle is stable.

18. The method of claim 17 wherein said step of determining if said ventricle is stable is performed by analyzing a ventricular rate.

19. The method of claim 18 wherein said ventricular rate is analyzed by analyzing the variability of R—R intervals.

20. The method of claim 17 further comprising the step of stabilizing said ventricle if said ventricle is found unstable, and then applying said therapy after said ventricle has been stabilized.

21. The method of claim 20 wherein said ventricle is stabilized by pacing said ventricle.

22. The method of claim 21 wherein said ventricle is beating at a certain rate when unstable, and wherein said ventricle is stabilized by applying pacing pulses to said ventricle to increase said certain rate until ventricle stability is achieved.

23. The method of claim 22 further comprising the step of decreasing said ventricular rate after the ventricle has been stabilized toward a minimum stabilized ventricular rate.

24. The method of claim 23 wherein said defibrillation pulses are applied at said minimum rate.

25. The method of claim 23 wherein said atrial defibrillation pulses are applied synchronously with or a predetermined time after one of said ventricular events.

* * * * *